United States Patent [19]
Robioneck

[11] Patent Number: 5,326,367
[45] Date of Patent: Jul. 5, 1994

[54] ENDOPROSTHESIS FOR A CANCER DAMAGED PELVIS

[75] Inventor: Bernd Robioneck, Kiel, Fed. Rep. of Germany

[73] Assignee: Howmedica GmbH, Schönkirchen, Fed. Rep. of Germany

[21] Appl. No.: 938,741

[22] Filed: Sep. 2, 1992

[30] Foreign Application Priority Data

Sep. 10, 1991 [DE] Fed. Rep. of Germany ... 9111221[U]

[51] Int. Cl.⁵ ............................................. A61F 2/34
[52] U.S. Cl. ................................................... 623/22
[58] Field of Search .......................... 623/16, 18, 22, 23

[56] References Cited

U.S. PATENT DOCUMENTS

| | | | |
|---|---|---|---|
| 3,720,959 | 3/1973 | Hohn | 623/16 |
| 3,803,641 | 4/1974 | Golyakhousky | 623/18 |
| 3,808,606 | 5/1974 | Tronzo | 623/16 |

FOREIGN PATENT DOCUMENTS

| | | | |
|---|---|---|---|
| 2809556 | 9/1979 | Fed. Rep. of Germany | 623/22 |
| 3027063 | 2/1982 | Fed. Rep. of Germany | . |
| 9111221 | 10/1991 | Fed. Rep. of Germany | . |
| 2578162 | 9/1986 | France | 623/22 |
| 2595241 | 9/1987 | France | 623/22 |
| 2651995 | 3/1991 | France | . |
| 8801491 | 3/1988 | World Int. Prop. O. | 623/22 |

*Primary Examiner*—David Isabella
*Attorney, Agent, or Firm*—Peter C. Richardson; Lawrence C. Akers; Raymond W. Augustin

[57] ABSTRACT

An endoprosthesis for cancer damaged hip bones has a recess in a distal portion to receive a prosthetic hip socket. The endoprosthesis includes an individual distal part and an individual proximal part which are secured to each other by means of a screw connection. The distal and the proximal part include mounting brackets for screwing the parts to the hip bone or, respectively, to a vertebra. In addition, the proximal and distal parts are shaped to positively inter-engage each other.

2 Claims, 2 Drawing Sheets

ENDOPROSTHESIS FOR A CANCER DAMAGED PELVIS

BACKGROUND OF THE INVENTION

1. Field of the Invention

The invention relates to an endoprosthesis for cancer damaged hip bones. More particularly it relates to a prosthetic pelvis made in two parts.

2. Description of the Prior Art

A variety of endoprostheses have been used to replace the damaged ball of the femur and/or the acetabular socket of the hip bone when these parts are damaged or deteriorate and do not properly function. In cancer damaged hip bones, a large portion of the bony structure of the hip bone is attacked by cancer and is thus incapable of supporting a prosthetic hip socket in the usual manner. In such cases a unique bone substitute must be formed which includes a recess in the distal portion to receive a prosthetic hip socket. The forming of individual endoprostheses of this type is costly and takes too long a time.

It is known to first form a model of the bone portion to be substituted using x-rays, in particular computer tomography, and then to form the endoprosthesis from the model.

SUMMARY OF THE INVENTION

The object of the present invention is to provide an endoprosthesis for cancer damaged hip bones which can be used in a wide variety of individual shapes of the hip bone.

The present invention utilizes the knowledge that it is standard procedure to have an x-ray photographic survey performed when cancer damaged parts lie within the region of the natural hip socket or close thereto. It is further important that the prosthetic recess for receiving the prosthetic hip socket finds sufficient support and is safely secured to the hip bone.

The endoprosthesis according to the invention provides for a unique structure, but allows for individual customized adjustment with respect to the dimensions of the hip bone. According to the invention, the endoprosthesis comprises a distal and a proximal part which can be rigidly secured together by screws. The distal as well as the proximal part include mounting extensions to be secured by screws to the hip bone or, alternately, to a vertebra. For vertebral use, preferably, the proximal part is secured to the fifth vertebra and to the sacrum.

The two-part structure of the endoprosthesis according to the present invention facilitates its fabrication in a die casting process, thus reducing fabrication costs. Furthermore, the surgical attachment of the prosthesis parts is simplified due to its bipartite structure. For example, after resecting certain bone portions of the pelvis, the proximal part is first fixed and then the distal part is secured to the proximal part, whereupon the proximal part is screwed to the vertebra.

For a safe connection between the distal and the proximal part, the invention provides for an interlaced connection. According to a further embodiment of the invention, both interlaced portions include interlocking elements, such as a nose, formed on the first part engaging a corresponding recess of the second part. The noses prevent a relative rotation of the parts even when a single screw only is used for connecting both parts. Preferably, a pair of screws is used and the heads thereof are preferably recessed.

According to a still further embodiment of the invention, the distal part of the prosthesis is formed to comprise a pair of supporting portions of which one engages a pubic bone branch and the other an ischium branch, each supporting portion including a securing bracket. The supporting portions thus define bridge portions between the pubic bone branch, or, respectively, the ischium branch remaining and the portion of the distal prosthesis part in which the acetabular recess is formed to receive the prosthesis hip socket.

According to a still further embodiment, the proximal part includes a pair of securing brackets of which one having a surface laterally engages the sacrum, and the other engages the vertebra in front leaving still a nerve passage. Each bracket preferably has a number of screw bores for receiving spongiosa screws to be secured to the associated vertebra.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
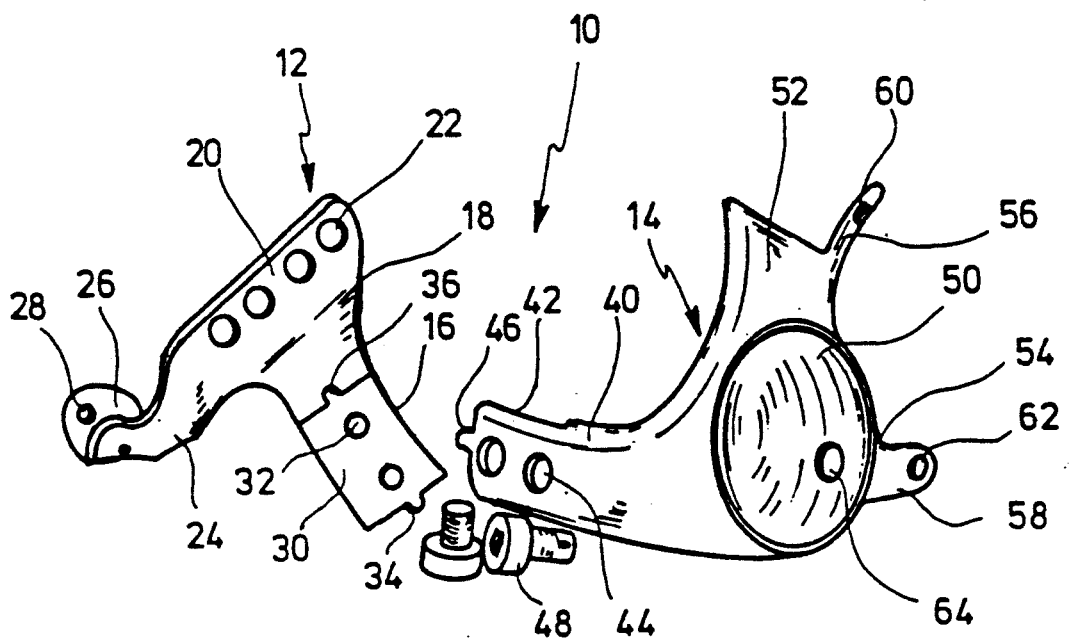
FIG. 1 is a perspective view of an endoprosthesis according to the invention.

Referring to FIGS. 1–4 there is shown an endoprosthesis 10 which comprises a first part 12 and a second part 14. Both parts 12 and 14 may be die cast and are made of biologically compatible material such as a cobalt chrome alloy. The mold is made in a known manner using computer tomography, for example, from a survey of the bone region to be replaced and making the mold according to the data obtained in this known way.

The first part 12 includes a plate-shaped portion merging via a curved portion 18 in a flat mounting bracket 20 which includes four holes 22 to receive bone screws (not shown). The plane of mounting bracket 20 extends at a small angle with respect to the plane of the plate portion 16. The mounting portion 20 extends beyond a bent portion 24 to a second curved mounting bracket 26 which also includes four holes 28 to receive bone screws (not shown). The plate portion 16 includes an extension 30 in which two holes 32 are provided. A rounded nose 34 i provided at the free end of the plate portion 16. A recess 36 which is complementary with respect to the nose 34 is formed on portion 18 at a shoulder of the extension 30.

The second part 14 comprises a plate portion 40 including an extension 42 including two holes 44. The extensions 30, 42 are complementarily shaped, and the nose 46 of the portion 40 engages the recess 36 when the extensions 30, 42 are mounted in overlapping relationship. Screws 48 are used to secure the plate portions 16, 40 together, wherein the screw heads are received in the holes 44.

Figure 2:
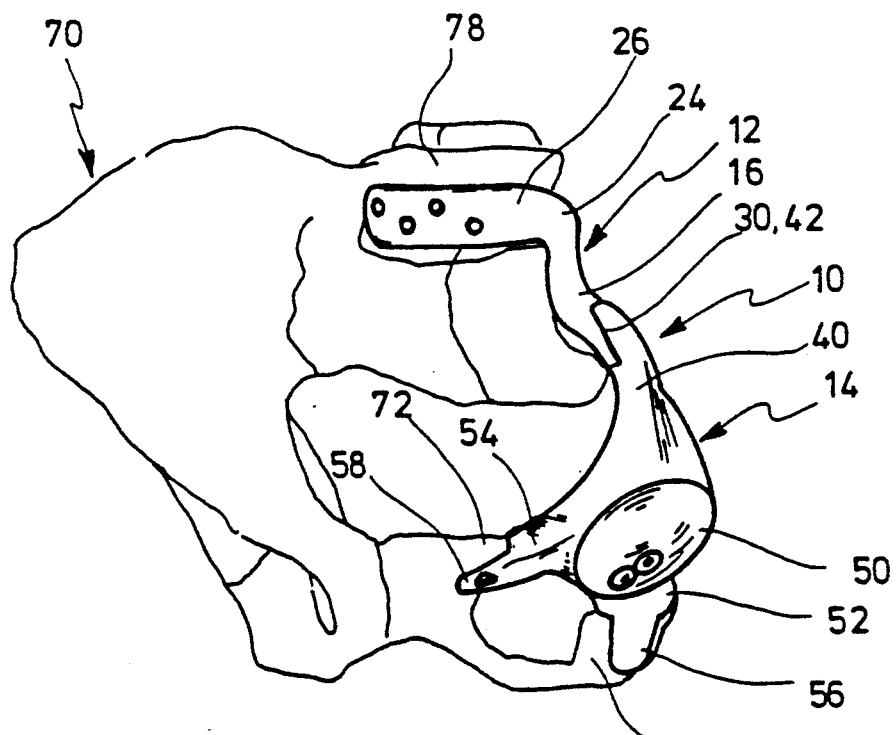
FIG. 2 is a perspective view of a part of a hip bone from the front including an endoprosthesis mounted thereon.
Figure 3:
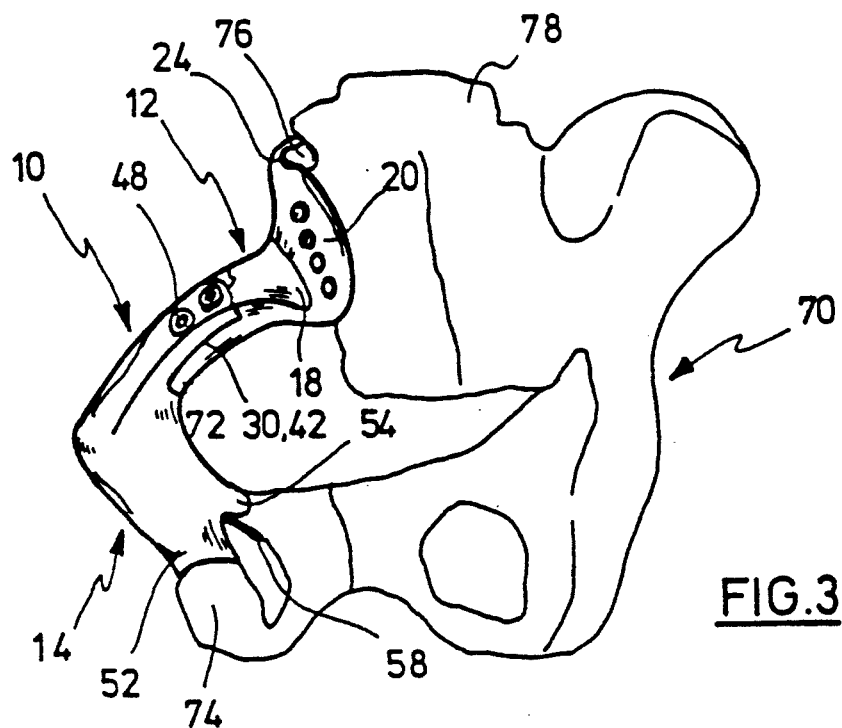
FIG. 3 is a view of the hip bone from the rear and a prosthesis mounted.
Figure 4:
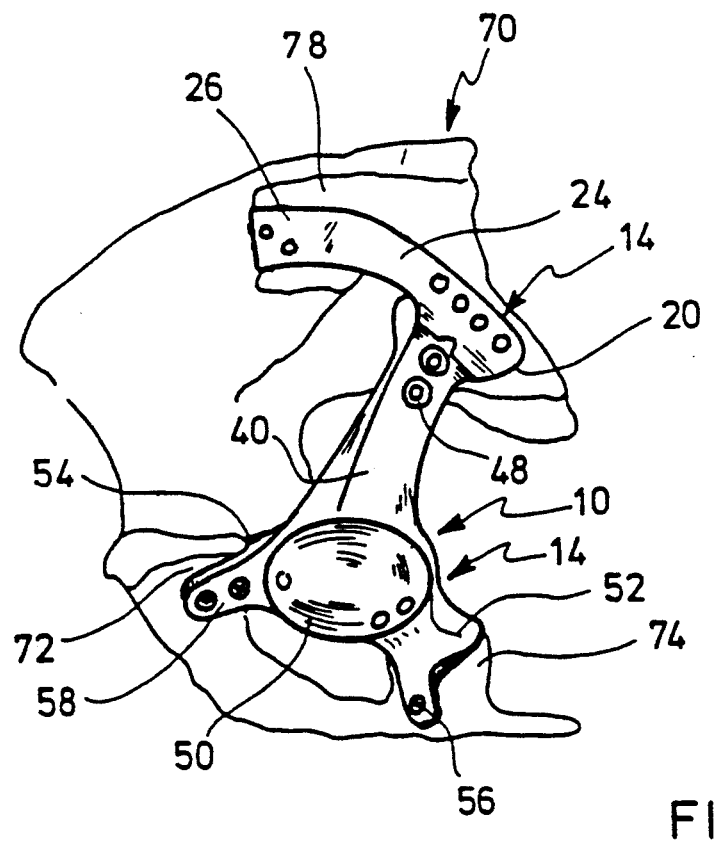
FIG. 4 is a left-hand view of a hip bone and a prosthesis mounted.

A recess 50 is provided to receive a prosthetic hip socket made of, for example, a suitable plastic material. Recess 50 is located in center region of the second part 14. A first supporting portion 52 and a second supporting portions 54 are provided and include lateral mounting brackets 56 and 58 respectively. Each mounting bracket has a hole 60 to receive a bone screw. Mounting brackets 56 and 58 are formed on the side of the recess 50 opposite the plate portion 40. The supporting portions 52, 54 are provided with obtuse ends and surfaces having a microspherical structure or bone ingrowth surfaces for facilitating attachment to the bone. A number of holes are provided for bone screws. Supporting portion 54 includes a hole 64 which opens into the recess 50. Supporting portion 52 may be provided with two holes as shown in FIG. 2. The holes receive screws for mounting the distal part to proper bone sections of the pelvis.

According to FIG. 2 a pelvis bone 70 is shown in a front view; the pubic bone and the ischium are resected on the left-hand side. Thus a pubic bone branch 72 and an ischium branch 74 remain after the resection. The surgical cut is selected such that the obtuse end of the supporting portions 52, 54 obtusely contacts the branches 72, 74. The mounting takes place through the mounting brackets 58 and 56. Furthermore, the supporting portions are secured by screws which are inserted through the holes opening into the recess 50.

In performing the surgical operation, the second part 14 is first mounted in the manner described and then the part 14 is screwed to the first part 12 using screws 48. The mounting bracket 20 thus laterally engages the correlated vertebra 78 (5th lumbar vertebra) which has to be shaped correspondingly. The mounting bracket is then secured to vertebra 78 by means of screws. The other mounting bracket 26 engages the front side of vertebra 78 and is likewise mounted by means of screws, as particularly shown in FIGS. 2 and 4. The arched portion 24 leaves space for a nerve channel 76.

While several examples of the present invention have been described, it is obvious that many changes and modifications may be made thereunto, without departing from the spirit and scope of the invention.

I claim:

1. An endoprosthesis for cancer damaged hip bones comprising:

a first portion for attachment to a vertebra, said first portion including a first and second mounting bracket, of which the first mounting bracket engages a vertebra laterally and the second mounting bracket engages the front of the vertebra, wherein a nerve passage is formed between said first and second mounting brackets, said first mounting bracket laterally engaging the vertebra being planar, and the second mounting bracket being arched;

a second portion for attachment to the pelvis and having a prosthetic acetabular portion for placement in an acetabular recess in the pelvis, said second portion including a pair of supporting portions, the first supporting portion having an end supported on a pubic bone branch and the second supporting portion having an end supported on an ischium branch, and that each of said ends including a mounting bracket, said ends of the first and second supporting portions of the second portion forming an obtuse angle therebetween and including a tissue ingrowth surface and said acetabular portion including at least one through bore opening into the acetabular recess for receiving a screw; and means for connecting said first and second portions, said means including interlocking portions which engage to prevent relative rotation between said first and second portions.

2. The endoprosthesis as set forth in claim 1 wherein the interlocking portions include complementary members including a nose element on one portion which engages a complementary recess in the other portion.

* * * * *